(12) United States Patent
Nakamura et al.

(10) Patent No.: US 9,599,903 B2
(45) Date of Patent: Mar. 21, 2017

(54) FOREIGN SUBSTANCE DETECTION METHOD, FOREIGN SUBSTANCE DETECTION APPARATUS, EXPOSURE METHOD, AND METHOD OF MANUFACTURING DEVICE

(71) Applicant: CANON KABUSHIKI KAISHA, Tokyo (JP)

(72) Inventors: Tadao Nakamura, Utsunomiya (JP); Yuji Kosugi, Utsunomiya (JP); Tomohisa Nakazawa, Nasu-gun (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 322 days.

(21) Appl. No.: 14/533,733

(22) Filed: Nov. 5, 2014

(65) Prior Publication Data
US 2015/0131065 A1     May 14, 2015

(30) Foreign Application Priority Data

Nov. 13, 2013  (JP) ................................. 2013-235385

(51) Int. Cl.
| | |
|---|---|
| G01N 21/00 | (2006.01) |
| G03B 27/32 | (2006.01) |
| G03B 27/52 | (2006.01) |
| G03F 7/20 | (2006.01) |
| G01N 21/95 | (2006.01) |
| G01N 21/94 | (2006.01) |
| G03F 9/00 | (2006.01) |
| G01S 17/48 | (2006.01) |

(52) U.S. Cl.
CPC .......... *G03F 7/2041* (2013.01); *G01N 21/94* (2013.01); *G01N 21/9501* (2013.01); *G03F 7/7065* (2013.01); *G03F 7/70916* (2013.01); *G03F 9/7026* (2013.01); *G01S 17/48* (2013.01)

(58) Field of Classification Search
CPC .... G01N 21/94; G01N 21/9501; G01S 17/48; G03F 7/2041; G03F 7/7065; G03F 7/70916; G03F 7/70925; G03F 9/7026
USPC .................. 355/30, 72, 77; 356/237.4, 237.5
See application file for complete search history.

(56) References Cited

U.S. PATENT DOCUMENTS

| | | | |
|---|---|---|---|
| 7,426,016 B2 | 9/2008 | Takada et al. | |
| 2011/0051112 A1 | 3/2011 | Nagasaka | |

FOREIGN PATENT DOCUMENTS

| | | |
|---|---|---|
| JP | 2006-140459 A | 6/2006 |
| JP | 2008-140814 A | 6/2008 |

*Primary Examiner* — Colin Kreutzer
(74) *Attorney, Agent, or Firm* — Rossi, Kimms & McDowell LLP

(57) ABSTRACT

A foreign substance detection method includes: judging the presence/absence of a foreign substance by measuring a surface condition of a substrate; measuring a surface condition of a second substrate different from the substrate upon replacing the substrate on the chuck with the second substrate, when it is judged in the judging that a foreign substance exists; and determining whether an adhering location of the foreign substance determined to exist in the judging is the substrate, based on a measurement result obtained in the measurement.

14 Claims, 9 Drawing Sheets

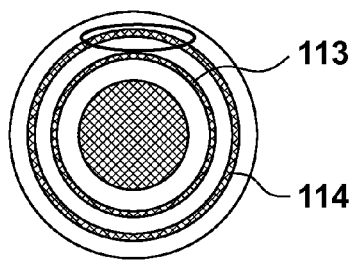
F I G. 2A
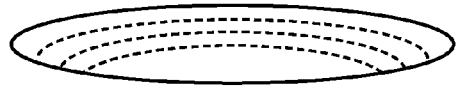
F I G. 2B
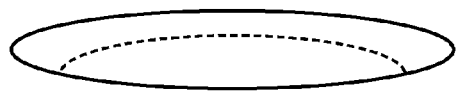
F I G. 2C
F I G. 3A
F I G. 3B
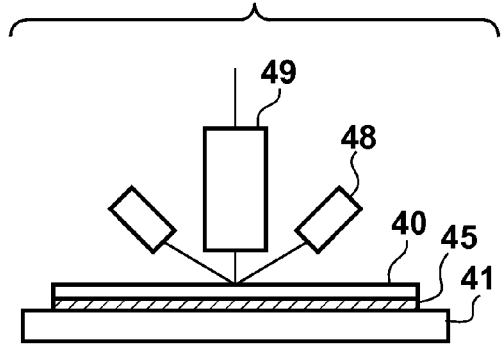
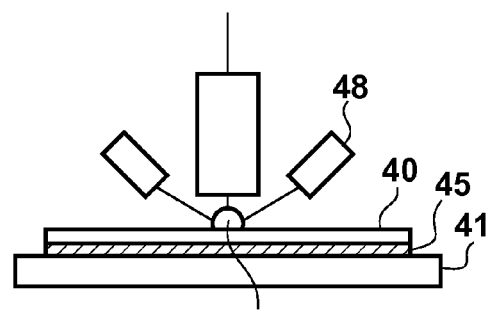
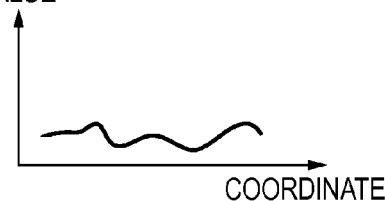
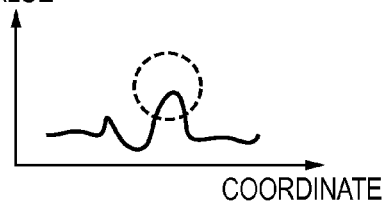

FIG. 8
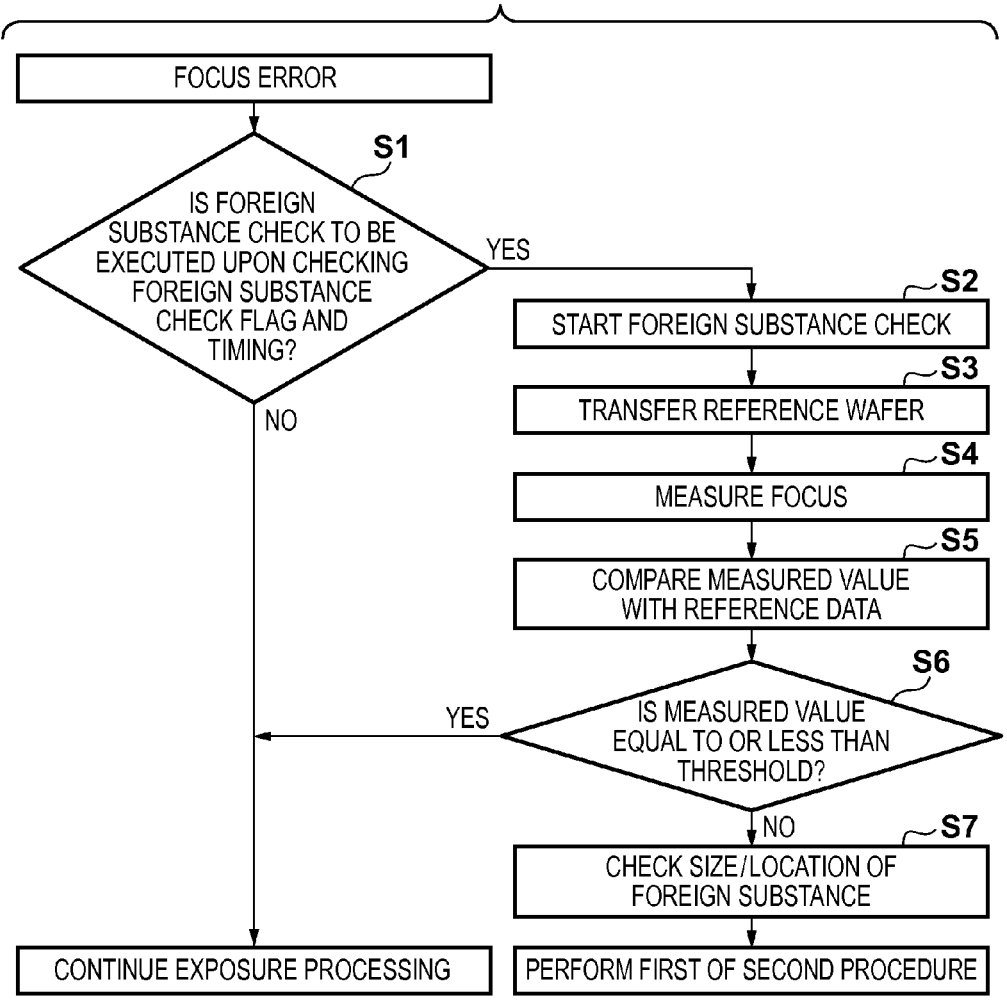
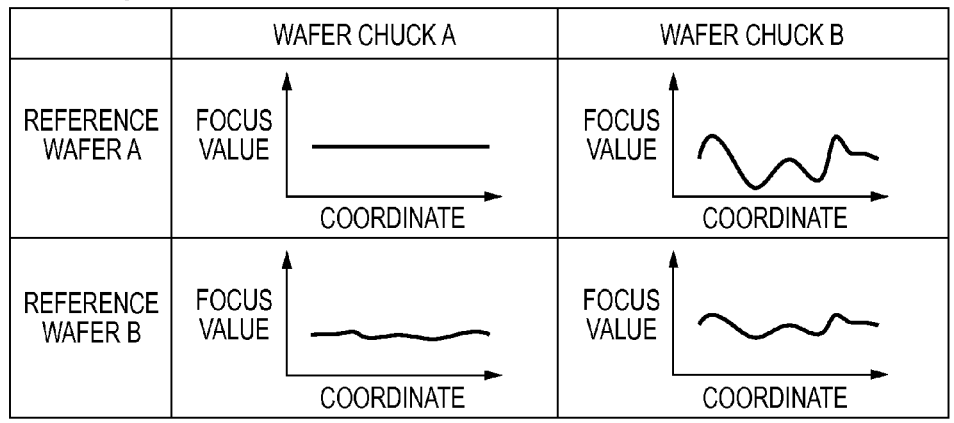

FOREIGN SUBSTANCE DETECTION METHOD, FOREIGN SUBSTANCE DETECTION APPARATUS, EXPOSURE METHOD, AND METHOD OF MANUFACTURING DEVICE

BACKGROUND OF THE INVENTION

Field of the Invention

The present invention relates to a foreign substance detection method, a foreign substance detection apparatus, an exposure method, and a method of manufacturing a device.

Description of the Related Art

The mainstream of recent semiconductor exposure apparatuses is a scanning exposure apparatus which exposes a substrate by relatively scanning the substrate and an original while irradiating a region smaller than a region to be exposed on the substrate with light. A scanning exposure apparatus generally has a focus detection system arranged before or after an exposure region to detect the height position of a substrate immediately before exposure. The apparatus controls a substrate stage to match the height of the substrate with the focal position of a projection optical system. In this case, the focus measurement value detected by the focus detection system tends to have a gradual trend in a normal process. When a steep change is observed in a focus measurement value, it often indicates that there is a foreign substance on a substrate or a foreign substance has adhered to a member (chuck) which chucks and holds the substrate. Extreme caution is given to foreign substances on the chuck, in particular, in a semiconductor manufacturing site, in which the chuck is periodically cleaned or replaced with a new one.

Japanese Patent Laid-Open No. 2006-140459 discloses the use of an immersion exposure apparatus to meet a requirement for further micropatterning of semiconductor devices. The immersion exposure apparatus disclosed in Japanese Patent Laid-Open No. 2006-140459 exposes a substrate while the air gap between at least partial region of the final surface of a projection optical system and a substrate on a substrate stage is filled with a liquid. The immersion exposure apparatus disclosed in Japanese Patent Laid-Open No. 2006-140459 has a detector provided on the substrate stage to detect foreign substances lower in specific gravity than the liquid or air bubbles existing in the liquid between the final surface of the projection optical system and the substrate by using an image sensor.

Japanese Patent Laid-Open No. 2008-140814 discloses a technique of judging the presence/absence of a foreign substance based on a detection result from a focus detection system which detects the height position of a substrate.

However, the immersion exposure apparatus disclosed in Japanese Patent Laid-Open No. 2006-140459 needs to be equipped with a dedicated detector including an image sensor for detecting foreign substances. In addition, in the exposure apparatus disclosed in Japanese Patent Laid-Open No. 2008-140814, the focus detection system performs measurement while a substrate is chucked on the chuck, and hence it is difficult to judge whether a foreign substance exists on the substrate or chuck. For this reason, the exposure apparatus disclosed in Japanese Patent Laid-Open No. 2008-140814 requires maintenance including the cleaning of the chuck every time a focus abnormal value is detected. This prolongs the maintenance time for the apparatus and affects productivity. For example, the chip production yield decreases.

SUMMARY OF THE INVENTION

The present invention provides a detection method of easily detecting the presence/absence of a foreign substance on a substrate.

The present invention in its one aspect provides a method of detecting presence/absence of a foreign substance on a substrate held on a stage through a chuck, the method comprising: a judging step of judging the presence/absence of a foreign substance by measuring a surface condition of the substrate; a measurement step of measuring a surface condition of a second substrate different from the substrate upon replacing the substrate on the chuck with the second substrate, when it is judged in the judging step that a foreign substance exists; and a determination step of determining whether an adhering location of the foreign substance determined to exist in the judging step is the substrate, based on a measurement result obtained in the measurement step.

Further features of the present invention will become apparent from the following description of exemplary embodiments with reference to the attached drawings.

BRIEF DESCRIPTION OF THE DRAWINGS

FIGS. 2A to 2C are views showing a nozzle formed in the exposure apparatus;

FIGS. 3A and 3B are views showing the surface position detector of the exposure apparatus;

FIG. 8 is a flowchart showing an example of operation in a foreign substance detection method;

DESCRIPTION OF THE EMBODIMENTS

[Exposure Apparatus]

Figure 1:
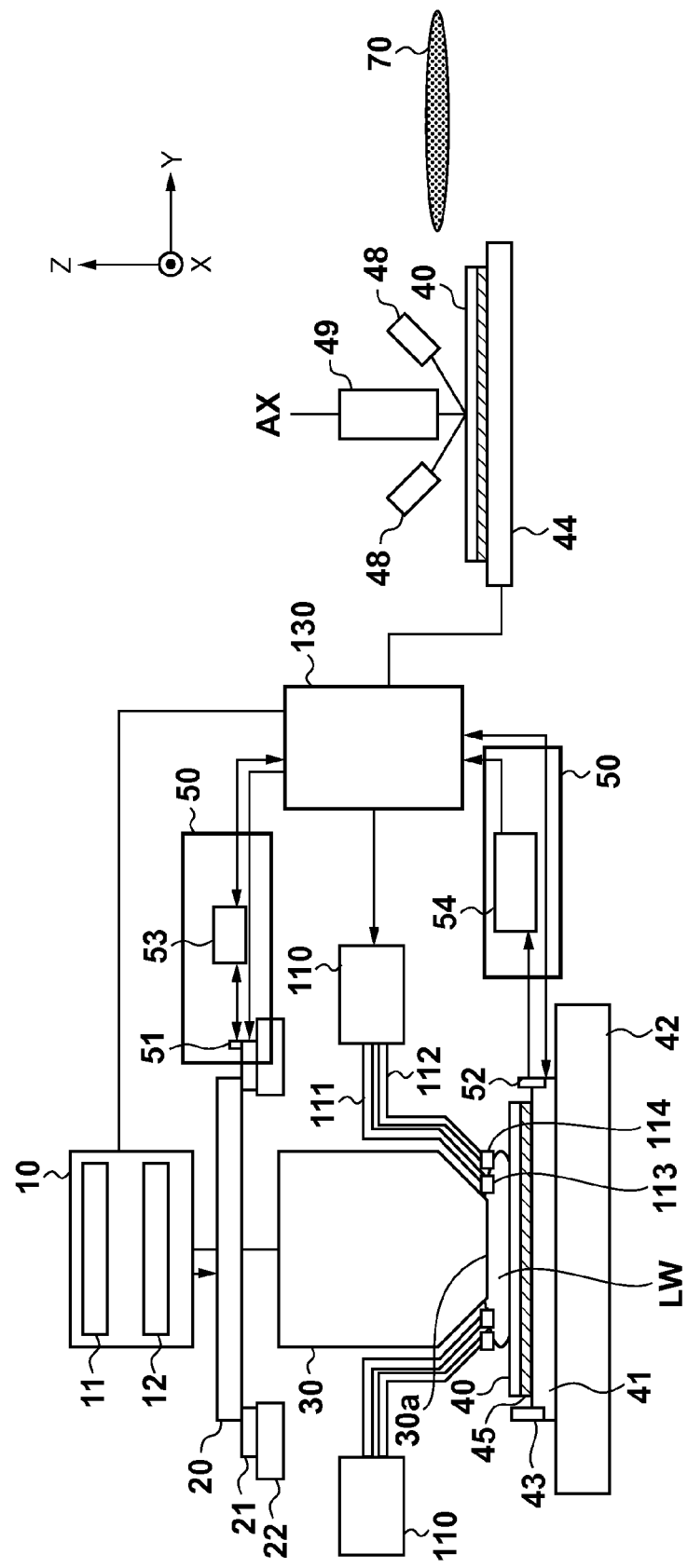
FIG. 1 is a schematic view showing an example of an exposure apparatus.

An embodiment of an exposure apparatus according to the present invention will be described. FIG. 1 shows the exposure apparatus exemplified by this embodiment. The embodiment uses a twin stage type immersion exposure apparatus which includes two substrate stages and exposes a substrate (wafer) 40 via the liquid (immersion liquid) LW supplied into the air gap between the final surface of a projection optical system 30 and the substrate 40. However, the exposure apparatus which can be used in the present invention is not limited to a twin stage type exposure apparatus or immersion exposure apparatus. In addition, the present invention is not limited to an exposure apparatus and can be generally applied to lithography apparatuses including a drawing apparatus which performs drawing on a substrate with a charged particle beam and an imprint apparatus which forms a pattern on a substrate by imprint processing.

The immersion exposure apparatus according to this embodiment exposes the substrate 40, upon projecting the circuit pattern formed on a reticle (mask) 20 onto the substrate 40, via the liquid LW supplied into the air gap between the substrate 40 and a final lens 30a of the projection optical system 30 which is nearest to the substrate 40. As a scheme for projecting the circuit pattern formed on the reticle 20 onto the substrate 40, for example, a step-and-scan scheme or step-and-repeat scheme is generally known. This embodiment will exemplify a step-and-scan immersion exposure apparatus.

As shown FIG. 1, an exposure apparatus 1 includes a reticle stage 21 on which an illumination system 10 and a reticle 20 are mounted, the projection optical system 30, and a stage (substrate stage) 41 which can move while holding the substrate 40. The exposure apparatus 1 also includes an auxiliary plate (same surface plate) 43, a distance measurement device 50, and a control unit 130. The auxiliary plate 43 is arranged around the substrate 40 and provided on the substrate stage 41 such that the surface of the auxiliary plate 43 is almost flush with the surface of the substrate 40. The illumination system 10 irradiates, with light, the reticle 20 on which a circuit pattern for transfer is formed, and includes a light source unit 11 and an illumination optical system 12. In this embodiment, as the light source unit 11, an ArF excimer laser with a wavelength of 193 nm is used. However, the light source unit 11 is not limited to an ArF excimer laser, and for example, a KrF excimer laser with a wavelength of about 248 nm or an F2 laser with a wavelength of about 157 nm may be used. The number of light sources to be used is not specifically limited.

The illumination optical system 12 is an optical system which illuminates the reticle 20. The reticle 20 is transferred from the outside of the exposure apparatus 1 by a reticle transfer system (not shown), and is driven while being supported on the reticle stage 21. The reticle 20 is made of, for example, quartz, and a circuit pattern to be transferred is formed on the reticle 20. Diffracted light emerging from the reticle 20 passes through the projection optical system 30 and is projected on the substrate 40. The reticle 20 and the substrate 40 are arranged in an optically conjugate relationship. The exposure apparatus 1 according to this embodiment is of the step-and-scan scheme. For this reason, the reticle 20 and the substrate 40 are scanned at a speed ratio corresponding to a reduction magnification ratio to project the pattern of the reticle 20 onto the substrate 40.

The reticle stage 21 is mounted on a surface plate 22. The reticle stage 21 supports the reticle 20 via a reticle chuck. A moving mechanism (not shown) and the control unit 130 perform movement control of the reticle stage 21. The moving mechanism (not shown) is formed from a linear motor or the like, and can move the reticle 20 in the X direction by driving the reticle stage 21. The projection optical system 30 forms diffracted light passing through the pattern formed on the reticle 20 into an image on the substrate 40. As the projection optical system 30, it is possible to use a refractive optical system constituted by only a plurality of lens elements, a catadioptric system including a plurality of lens elements and at least one concave mirror, or the like.

The substrate 40 is transferred from the outside of the exposure apparatus 1 by a substrate transfer system (not shown) and is chucked and held by a chuck (wafer chuck) 45 on the substrate stage 41. The substrate 40 is, for example, a wafer in this embodiment but widely includes a glass substrate and other objects to be exposed. The substrate 40 is coated with a photoresist. The substrate stage 41 is mounted on a surface plate 42 and holds the substrate 40 through the wafer chuck 45. The substrate stage 41 has a function of adjusting the position of the substrate 40 in the up-and-down direction (vertical direction), the rotating direction, and the tilt, and is controlled by the control unit 130.

At the time of exposure, the control unit 130 controls the substrate stage 41 so as to always match the surface of the substrate 40 with the focal plane of the projection optical system 30 with high accuracy. The distance measurement device 50 measures the position of the reticle stage 21 and the two-dimensional position of the substrate stage 41 in real time via reference mirrors 51 and 52 and laser interferometers 53 and 54. The measurement results obtained by the distance measurement device 50 are transferred to the control unit 130, and the reticle stage 21 and the substrate stage 41 are driven at a constant speed ratio under the control of the control unit 130 for positioning and synchronization control.

The auxiliary plate 43 is a plate for the formation of a surface flush with the surface of the substrate 40. The auxiliary plate 43 is arranged on the substrate stage 41 and around the substrate 40 at almost the same level as the surface of the substrate. The control unit 130 supplies a liquid LW from a liquid supply and recovery unit 110 into the air gap between the surface of the substrate 40 and the final lens 30a of the projection optical system 30 through a supply tube 111. The control unit 130 recovers the liquid LW into the liquid supply and recovery unit 110 through a recovery tube 112 for recovering the liquid LW.

The liquid LW is formed from a source water supplied from a source water supply source (not shown) upon reducing impurities such as metal ions, fine particles, and organic substances contained in the water. The liquid LW is supplied to a deaeration device (not shown) and controlled at a predetermined temperature. The liquid LW is selected from liquids which do not much absorb exposure light and have refractive indices as high as possible. More specifically, as the liquid LW, pure water, functional water, fluoride liquid (for example, fluorocarbon), organic liquid, or the like is used. In addition, the liquid LW is used after dissolved gases are sufficiently removed by using the deaeration device. Furthermore, the liquid LW may be a liquid containing water with a slight amount of additive or a hydrocarbon-based organic liquid. The control unit 130 supplies and recovers the liquid LW into and from the air gap between the final lens 30a of the projection optical system 30 and the substrate 40 via the supply tube 111, the recovery tube 112, a liquid supply nozzle 113, and a liquid recovery nozzle 114.

FIG. 2A is a plan view showing the liquid supply nozzle 113 and the liquid recovery nozzle 114. FIGS. 2B and 2C each are an enlarged view of an elliptic region in which the liquid recovery nozzle 114 in FIG. 2A exists. The liquid immersion region filled with the liquid LW is the region surrounded by the liquid recovery nozzle 114 so as to include a projection region and locally formed at a portion on the substrate 40. In this embodiment, the projection region of the projection optical system 30 is set to have a rectangular shape with the X-axis direction being the longitudinal direction. However, this region may be set to have a rectangular shape with the Y-axis direction being the longitudinal direction. In addition, as the liquid supply nozzle 113 and the liquid recovery nozzle 114 of the exposure apparatus, circular members are used. However, the shapes of the nozzles are not limited to this. For example, even if the nozzles have rectangular shapes, the same effects as those of this embodiment can be obtained.

The liquid supply and recovery unit 110 has a structure for both supplying and recovering the liquid LW, and is controlled by the control unit 130. In addition, the liquid supply and recovery unit 110 supplies and recovers the liquid LW at the time of the movement of the substrate stage 41. With this operation, the liquid supply and recovery unit 110 constantly maintains the state of the liquid LW by, for example, removing dissolved gases or impurities in the liquid LW existing in the liquid immersion region. The control unit 130 includes a CPU and a memory (neither of which is shown), and controls the operation of the exposure apparatus 1. The control unit 130 is electrically connected to the illumination system 10, a moving mechanism (not shown) for the reticle stage 21, a moving mechanism (not shown) for the substrate stage 41, and the liquid supply and recovery unit 110. The CPU may be any type of processor such as an MPU, and controls the operation of each unit. The memory is constituted by a ROM and a RAM, and stores firmware which operates the exposure apparatus 1.

For example, when performing exposure, the control unit 130 may control the supply and recovery of the liquid LW by switching the flowing directions of the liquid LW to be supplied in accordance with the movement of the substrate stage 41. In addition, when performing exposure, the control unit 130 may perform control to always supply and recover a predetermined amount of liquid LW. The liquid supply and recovery unit 110 supplies the liquid LW via the supply tube 111 and the liquid supply nozzle 113, and recovers the liquid LW via the recovery tube 112 and the liquid recovery nozzle 114.

The exposure apparatus according to this embodiment further includes another substrate stage 44 in addition to the substrate stage 41. In addition, an alignment scope 49 and a surface position detector (focus sensor) 48 which executes focus measurement are arranged on a measurement station on which the substrate stage 44 is placed. The substrate stage 44 is connected to the control unit 130 and performs comprehensive driving operation and control. Note that the principle of focus measurement in this embodiment is based on an oblique incident optical system generally known in the field of semiconductor exposure apparatuses. That is, this scheme makes light from an LED or the like enter the measurement position on the substrate surface obliquely with respect to an optical axis AX and makes a detector such as a CCD receive reflected light from the substrate. A change in the position of the substrate surface in the optical axis AX direction is measured as a change in incident position on the detector, and is output as a focus measurement result from the surface position detector 48.

The alignment scope 49 and the surface position detector 48 arranged on the substrate stage 44 measure the surface condition of a substrate such as the distortion amount and wavy shape of the substrate. The alignment scope 49 and the surface position detector 48 constitute a measurement device which measures the surface conditions of the substrate 40 and the wafer chuck 45. While the substrate 40 held by the substrate stage 41 is exposed under the projection optical system 30 on an exposure station, the alignment scope 49 and the surface position detector 48 measure the surface condition (roughness, distortion amount, and the like) of the substrate 40 held by the substrate stage 44. Such a twin-stage system can improve throughput by measuring the next substrate 40 while measuring the substrate 40. The twin-stage system causes the exposure station to perform exposure based on the result obtained by measuring the surface condition of the substrate 40 using the measurement station.

Liquid droplets sometimes stay in the immersion exposure apparatus after the completion of exposure because of insufficient recovery of the liquid. The residual liquid droplets sometimes vary a measurement result on the surface condition of the substrate 40. FIGS. 3A and 3B show how a foreign substance (a liquid droplet or particle) stays on the substrate and focus values. FIG. 3A shows the measurement values obtained by the surface position detector 48 while no foreign substance exists on the wafer chuck 45 and the substrate 40. In general, variations in focus value often exhibit a gradual tendency. FIG. 3B shows a case in which a foreign substance exists on the substrate 40. In this case, abnormality is often observed in the peak value of the focus values measured by the surface position detector 48. Therefore, an abnormal value on the substrate 40 is detected by setting a threshold for focus variations.

Figure 4A:
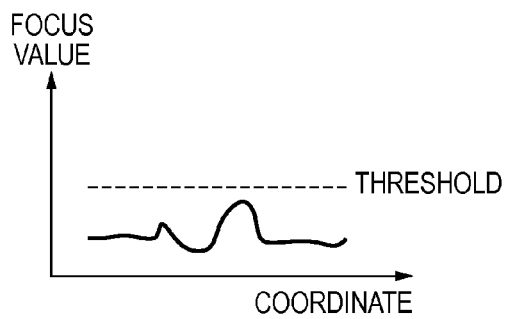
FIGS. 4A and 4B are graphs showing focus measurement values and a threshold.
Figure 4B:
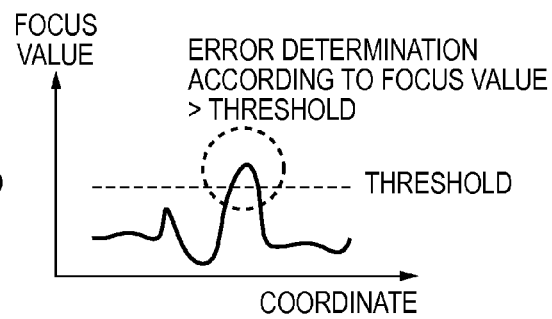

FIGS. 4A and 4B each show the relationship between focus measurement values and a threshold. Referring to FIG. 4A, the focus measurement values measured by the surface position detector 48 are smaller than a threshold. For this reason, the control unit 130 judges that there is no abnormal value. Referring to FIG. 4B, since the focus measurement value measured by the surface position detector 48 exceeds the threshold, it is judged that the value is regarded as an abnormal value, and an error has occurred. When an error has occurred, in general, exposure processing is stopped or an error/warning message is transmitted. There is available a method of continuing exposure processing.

Figure 5A:
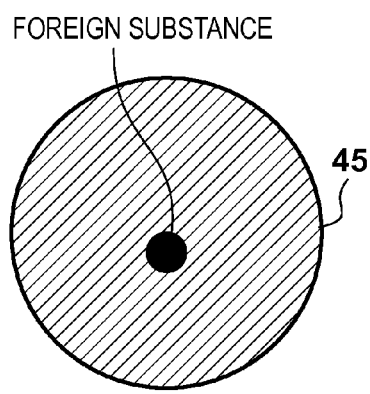
FIGS. 5A to 5C are views showing a foreign substance on a chuck and focus measurement values.
Figure 5B:
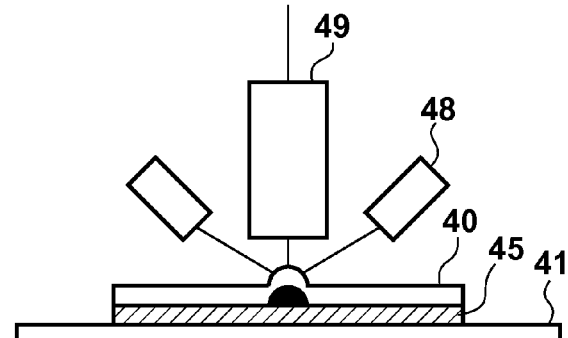
Figure 5C:
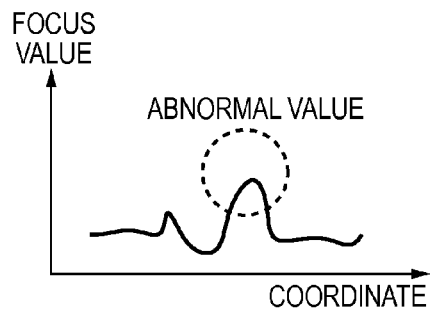

FIG. 5A shows a case in which a foreign substance exists on the wafer chuck 45. In this case, when the wafer chuck 45 chucks and holds the substrate 40, the substrate 40 is lifted by the foreign substance, as shown in FIG. 5B. For this reason, in this state, when the surface position detector 48 performs focus measurement, an abnormal value is observed, as shown in FIG. 5C. However, with only the focus measurement value obtained by the surface position detector 48, although the presence of a foreign substance can be detected, it cannot be judged whether the foreign substance adheres onto the substrate 40 or the wafer chuck 45.

A method of judging whether a foreign substance adheres onto the substrate 40 or the wafer chuck 45 will be described concerning a problem in this embodiment. A process of making advance preparation will be described. One or more reference wafers (second substrates) are prepared on the apparatus. Surface condition data as a reference which is a combination of the reference wafer and the wafer chuck 45 is stored. As the reference wafer used in this embodiment, it is possible to use a lid wafer for constant liquid immersion or SFW (Super Flatness Wafer). In addition, although a reference wafer is accommodated in the apparatus by an MC (Maintenance Carrier), the reference wafer may be transferred from an FOUP or inline system.

Figure 6:
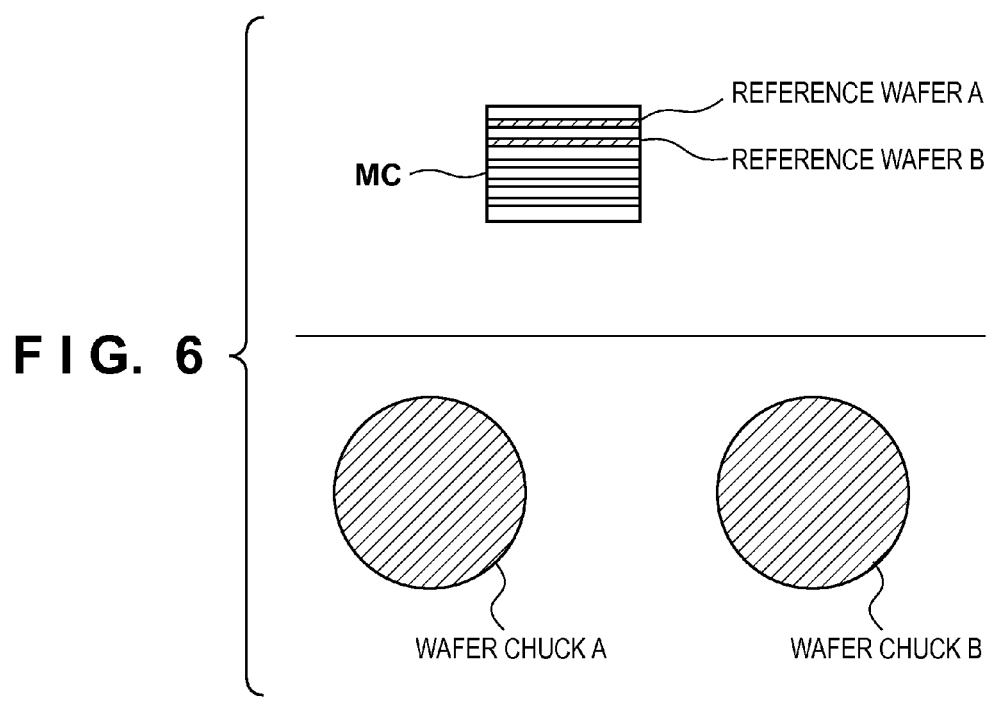
FIG. 6 is a schematic view of reference wafers and chucks.

The MC shown in FIG. 6 can accommodate five wafers and now are accommodating only two reference wafers A and B. Although reference wafers A and B are respectively accommodated in the first and second slots of the MC, the types and number of reference wafers are not limited to them. In this embodiment, since this embodiment is based on the use of a twin-stage exposure apparatus, there are two chucks, namely wafer chuck A and wafer chuck B, as the wafer chucks 45. When using a single stage, one wafer chuck 45 is used.

Figure 7:
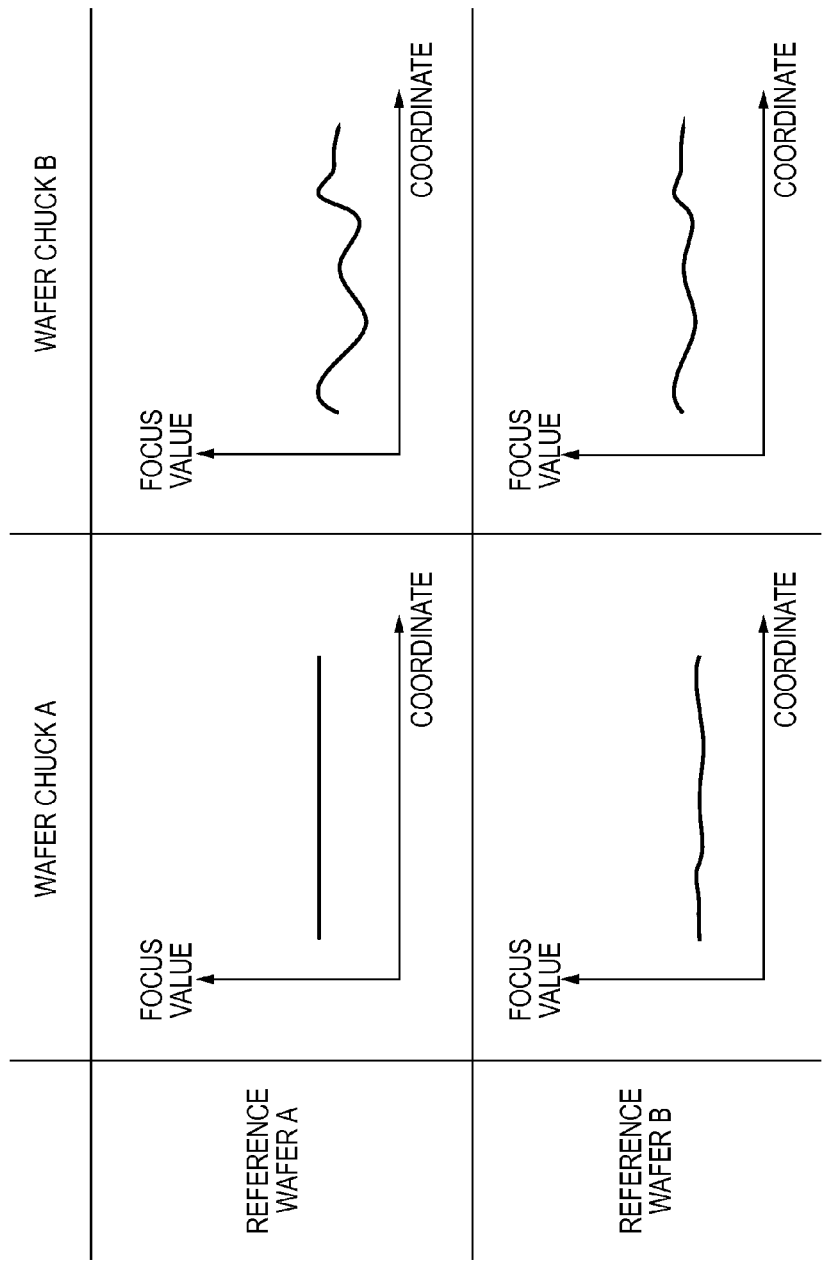
FIG. 7 is a view showing focus reference data of reference wafers (combinations of chucks and wafers)

Surface condition data is then obtained when reference wafer A is mounted on wafer chuck A. As described above, surface condition data is measured by using the surface position detector 48. At this time, since this data is reference data, it is possible to obtain surface condition data before a foreign substance adheres to the wafer chuck 45 or immediately after the cleaning or replacement of the wafer chuck 45. Likewise, the surface condition data of reference wafer A and wafer chuck B, reference wafer B and wafer chuck A, and reference wafer B and wafer chuck B are obtained, and the data are stored as reference data in advance. In addition, these reference data can be updated at an arbitrary timing. FIG. 7 illustrates combinations of reference wafers A and B and wafer chucks A and B, and surface condition data. In addition, since this embodiment used two reference wafers and two wafer chucks, the reference data of four surface conditions were obtained. However, the embodiment is not limited to this number of combinations.

The surface position detector 48 measures the surface condition of the process wafer (substrate) 40 as a focus value while the exposure apparatus is performing exposure processing. The control unit 130 judges the presence/absence of a foreign substance based on the measurement result (judging step). The control unit 130 forms a processing unit which determines the adhering location of the foreign substance. In addition, the alignment scope 49, the surface position detector 48, and the control unit 130 constitute a detector which detects the presence/absence of a foreign substance. FIG. 8 shows a procedure for a foreign substance check, which discriminates, upon detection of an abnormal value in the measurement result obtained by the surface position detector 48, whether the abnormal value is due to the influence of a foreign substance on the process wafer 40 or on the wafer chuck 45. It is possible to set the timing of a foreign substance check in FIG. 8 for each recipe. For example, there are available a method of transferring a reference wafer and performing a foreign substance check immediately after the occurrence of an error, a method of performing a foreign substance check after the completion of exposure processing on a lot basis, and a method of performing a foreign substance check when an error continuously occurs over a predetermined number of wafers. The control unit 130 checks in step S1 whether a foreign substance check timing has come. If YES in step S1, the control unit 130 starts a foreign substance check in step S2.

Figure 9A:
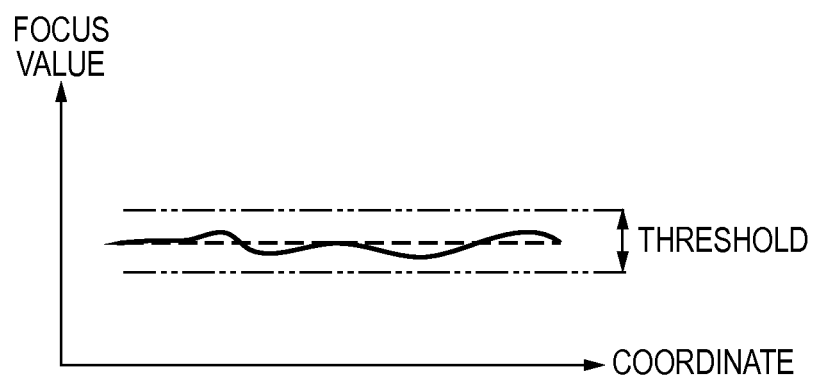
FIGS. 9A and 9B are graphs showing focus measurement values, reference data, and a threshold.
Figure 9B:
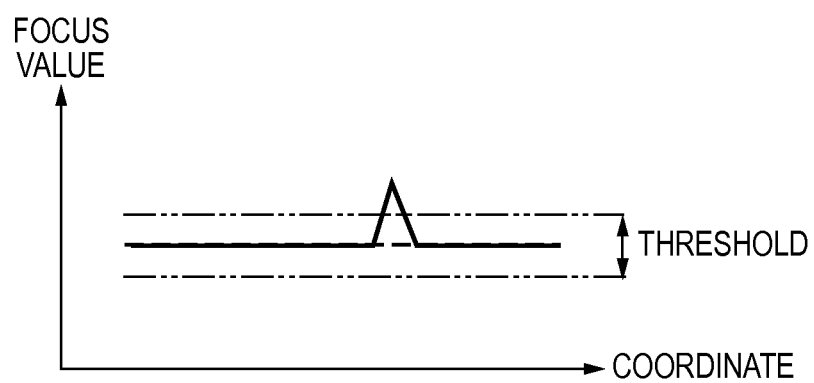

In step S3, the control unit 130 transfers a reference wafer from the MC to the wafer chuck 45 on which focus abnormality has been observed. Although this embodiment has exemplified the case in which reference wafer A is transferred to the wafer chuck 45, reference wafer B may be transferred. The control unit 130 causes the wafer chuck 45 to chuck and hold reference wafer A, and causes the surface position detector 48 to execute focus measurement (step S4). The control unit 130 then calculates the difference between the obtained surface condition data and the surface condition data (reference data) stored in advance (step S5). FIGS. 9A and 9B illustrate such data. When the difference is equal to or less than the threshold as shown in FIG. 9A, the control unit 130 determines that a foreign substance has stayed on the process wafer 40 on which a focus measurement error has occurred in step S6 (judging step), and continues exposure processing. When the difference is equal to or more than the threshold as shown in FIG. 9B, the control unit 130 determines that a foreign substance has adhered onto the wafer chuck 45 or reference wafer A (step S6). In this case, the threshold used for judgment can be arbitrarily set, and in general can be set in a range wider than that of reproducibility. In step S7, the control unit 130 estimates the size of the foreign substance and its coordinates (position) on the substrate from the difference data. The size of the foreign substance can be estimated from the absolute value of the focus measurement value. The position of the foreign substance can be estimated from the coordinate on the abscissa. If the control unit 130 determines in step S6 that a foreign substance adheres onto the wafer chuck 45 or reference wafer A, the process shifts to the first or second procedure after step S7 to determine whether the adhering location of the foreign substance is the wafer chuck 45.

[First Procedure]

Figure 10:
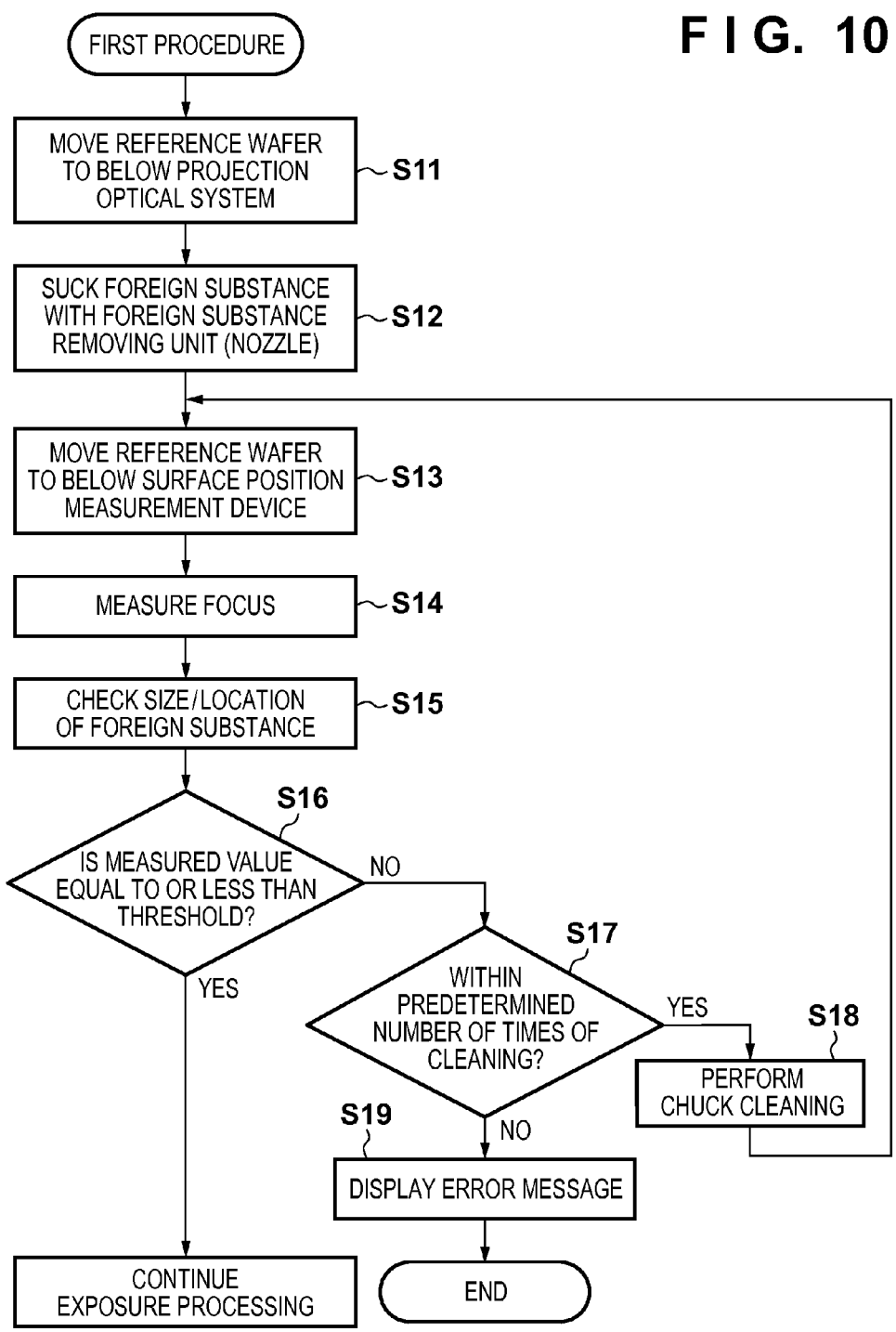
FIG. 10 is a flowchart showing an example of operation in the foreign substance detection method.

FIG. 10 shows the first procedure for determining whether the adhering location of a foreign substance is the wafer chuck 45. This embodiment exemplifies a case in which an immersion nozzle is used as a unit which removes a foreign substance. However, the embodiment is not limited to the immersion nozzle. In step S11, the control unit 130 drives the substrate stage 41 to move reference wafer A to below the projection optical system 30. The liquid LW exists in the air gap between the final lens 30a of the projection optical system 30 and the substrate stage 41. The liquid LW is circulated by the liquid supply nozzle 113 and the liquid recovery nozzle 114. In step S12, the control unit 130 moves reference wafer A to below the projection optical system 30 and tries to remove the foreign substance by suction. The place to which the foreign substance adheres can be estimated from a focus measurement value. The foreign substance can be efficiently removed in a short period of time by intensively sucking the place to which the foreign substance adheres on reference wafer A.

Subsequently, the control unit 130 moves reference wafer A to below the surface position detector 48 again (step S13), and obtains surface condition data (step S14). If the foreign substance observed before foreign substance removal processing has been removed, the control unit 130 determines that the foreign substance is adhered onto reference wafer A. If the foreign substance has not been removed, the control unit 130 determines that the foreign substance is adhering onto the wafer chuck 45 (step S16). If a focus measurement error occurs due to reference wafer A, it is possible to continue exposure processing without executing chuck cleaning. If a foreign substance is adhering onto the wafer chuck 45, the control unit 130 causes a chuck cleaning unit 70 shown in FIG. 1 to clear the wafer chuck 45 (step S18). In this embodiment, the chuck cleaning unit 70 is arranged near the surface position detector 48. However, the chuck cleaning unit 70 may be arranged near the projection optical system 30. It is possible to intensively execute cleaning in a short period of time by intensively cleaning the place where a foreign substance is recognized based on the focus measurement value.

After the chuck cleaning, surface condition data is obtained again to check a foreign substance adhering state again. If no foreign substance is observed after the cleaning, the control unit 130 determines that the foreign substance has been removed from the wafer chuck 45 by the cleaning. If the foreign substance has not been removed, the control unit 130 executes cleaning again. If the foreign substance cannot be removed even by repeating cleaning a predetermined number of times in step S17, the control unit 130 terminates the processing upon displaying an error message in step S19. The error message to be displayed at this time is, for example, a message prompting to replace the chuck. The predetermined number of times of cleaning can be arbitrarily set. Subsequently, the exposure apparatus is restored by executing cleaning using a different unit and replacing the chuck.

[Second Procedure]

Figure 11:
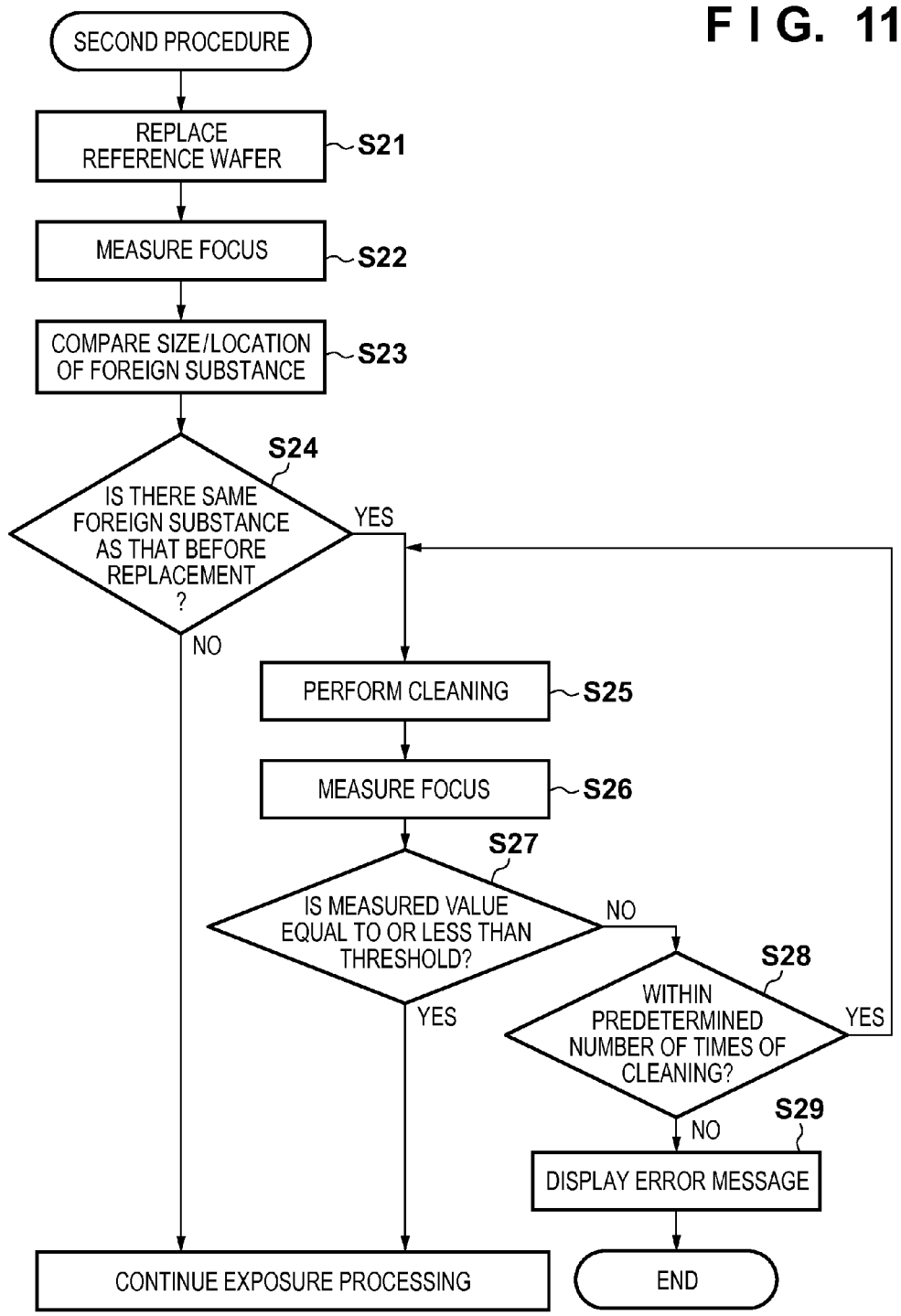
FIG. 11 is a flowchart showing an example of operation in the foreign substance detection method.

FIG. 11 shows another procedure for determining whether the adhering location of a foreign substance is the wafer chuck 45. In this case, the control unit 130 returns reference wafer A onto the maintenance carrier, and transfers a different reference wafer (third substrate) B onto the wafer chuck 45 (step S21). Thereafter, the control unit 130 causes the surface position detector 48 to obtain surface condition data again (step S22), and calculates the difference between the data and the reference data which is a combination of reference wafer B and the wafer chuck 45 and is stored in the apparatus in advance (step S23). If the foreign substance observed on reference wafer A is not observed on reference wafer B in step S24, the control unit 130 determines that a foreign substance has been on reference wafer A, and continues exposure processing without executing cleaning.

If a foreign substance is observed at the same location on reference wafer B as that on reference wafer A in step S24, the control unit 130 determines that the focus abnormality has been caused by the foreign substance on the wafer chuck 45, and executes cleaning of the wafer chuck 45 upon unloading reference wafer B (step S25). After the chuck cleaning, the control unit 130 transfers reference wafer A or B again, and obtains a focus measurement value (step S26). The control unit 130 then calculates the difference between the data and the reference data, and compares the difference with a threshold (step S27). If the cleaning is properly completed, since a value smaller than the threshold is output, it is possible to continue exposure processing. If the foreign substance on the wafer chuck 45 cannot be removed after the cleaning, the control unit 130 repeats cleaning (step S25), focus measurement (step S26), and a foreign substance check (step S27) a predetermined number of times. If this processing is not properly completed within the predetermined number of times, the control unit 130 outputs an error message indicating a chuck cleaning error or prompting to replace the chuck (step S29).

In the first procedure, foreign substances having the same size are sometimes observed on the same wafer chuck 45 at different places, depending on the combination of reference wafer A and the wafer chuck 45 and the combination of reference wafer B and the wafer chuck 45. In this case, in this embodiment, it is determined that the foreign substance on the wafer chuck 45 had moved when the reference wafer was replaced, and the wafer chuck 45 is cleaned. However, the embodiment is not limited to this.

As has been described above, after a foreign substance such as an immersion liquid or dust has adhered, it is determined first whether the adhering location of the foreign substance is the substrate 40. It is then determined whether the adhering location of the foreign substance is the wafer chuck 45. Subsequently, the wafer chuck 45 is cleaned only after it is determined that the adhering location of the foreign substance is the wafer chuck 45. This made it possible to implement quick recovery and improve productivity and maintenance performance, even if a foreign substance was detected.

[Method of Manufacturing Device]

A method of manufacturing a device (for example, a semiconductor device or liquid crystal display device) according to an embodiment of the present invention will be described. The semiconductor device is manufactured through a pre-process of forming an integrated circuit on a wafer (substrate), and a post-process of completing, as a product, an integrated circuit chip on the wafer that has been formed in the pre-process. The pre-process includes a step of exposing a wafer coated with a photosensitive agent by using the above exposure apparatus, and a step of developing the wafer exposed in the preceding step. The post-process includes an assembly step (dicing and bonding) and a packaging step (encapsulation). The liquid crystal display device is manufactured through a process of forming a transparent electrode. The process of forming a transparent electrode includes a step of applying a photosensitive agent to a glass substrate on which a transparent conductive film is deposited, a step of exposing the glass substrate coated with the photosensitive agent by using the above exposure apparatus, and a step of developing the glass substrate. According to the method of manufacturing a device according to this embodiment, a higher-quality device than a conventional one can be manufactured.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-235385, filed Nov. 13, 2013, which is hereby incorporated by reference herein in its entirety.

What is claimed is:

1. A method of detecting presence/absence of a foreign substance on a substrate held on a stage through a chuck, the method comprising:
    a judging step of judging the presence/absence of a foreign substance by measuring a surface condition of the substrate;
    a measurement step of measuring a surface condition of a second substrate different from the substrate upon replacing the substrate on the chuck with the second substrate, when it is judged in the judging step that a foreign substance exists; and
    a determination step of determining whether an adhering location of the foreign substance determined to exist in the judging step is the substrate, based on a measurement result obtained in the measurement step.

2. The method according to claim 1, wherein in the determination step, it is determined whether the adhering location of the foreign substance is the substrate, based on surface condition data of the second substrate measured in the measurement step and data of a surface condition of the second substrate held by the chuck, which is obtained in advance while no foreign substance exists.

3. The method according to claim 1, wherein if it is determined in the judging step that a foreign substance exists, with respect to another substrate which belongs to the same lot and to which the same processing is performed as those of a substrate on which the foreign substance is determined to exist, the measurement step is performed without performing the processing.

4. The method of according to claim 1, wherein if it is determined in the judging step that a foreign substance exists, with respect to all substrates which belong to the same lot and to which the same processing is performed as those of a substrate on which the foreign substance is determined to exist, the measurement step is performed after performing the processing.

5. The method according to claim 1, wherein the measurement step is performed if it is judged that a foreign substance continuously exists on a predetermined number of substrates.

6. The method according to claim 1, the method further comprising a second determination step of determining whether an adhering location of a foreign substance is the chuck, if it is determined in the determination step that the adhering location of the foreign substance is not the substrate.

7. The method according to claim 6, wherein the second determination step includes:
a step of measuring a surface condition of a third substrate different from the substrate and the second substrate upon replacing the second substrate on the chuck with the third substrate; and
a step of determining, based on a measurement result in the step, whether an adhering location of a foreign substance is the chuck.

8. The method according to claim 6, wherein the second determination step includes:
a step of measuring a surface condition of the second substrate again upon cleaning a surface of the second substrate; and
a step of determining, based on a measurement result in the step, whether an adhering location of a foreign substance is the chuck.

9. The method according to claim 6, the method further comprising a chuck cleaning step of cleaning a surface of the chuck if it is determined in the second determination step that the adhering location of the foreign substance is the chuck.

10. The method according to claim 9, wherein it is judged upon measurement of a surface condition of the chuck whether a foreign substance is removed after the surface of the chuck is cleaned in the chuck cleaning step, and the surface of the chuck is cleaned a predetermined number of times, if it is determined that the foreign substance is not removed.

11. The method according to claim 9, the method further comprising a step of displaying an error if it is determined that the foreign substance is not removed in the chuck cleaning step.

12. A method of exposing a substrate held on a stage through a chuck, the method comprising a detection step of detecting presence/absence of a foreign substance on the substrate,
wherein the detection step includes:
judging the presence/absence of a foreign substance by measuring a surface condition of the substrate;
measuring a surface condition of a second substrate different from the substrate upon replacing the substrate on the chuck with the second substrate, when it is judged in the judging that a foreign substance exists; and
determining whether an adhering location of the foreign substance determined to exist in the judging is the substrate, based on a measurement result obtained in the measuring.

13. A method of manufacturing a device, the method comprising:
an exposure step of exposing a substrate held on a stage through a chuck;
a step of developing the exposed substrate; and
a step of processing the developed substrate to manufacture the device,
wherein the exposure step includes a detection step of detecting presence/absence of a foreign substance on the substrate, and
the detection step includes:
judging the presence/absence of a foreign substance by measuring a surface condition of the substrate;
measuring a surface condition of a second substrate different from the substrate upon replacing the substrate on the chuck with the second substrate, when it is judged in the judging that a foreign substance exists; and
determining whether an adhering location of the foreign substance determined to exist in the judging is the substrate, based on a measurement result obtained in the measuring.

14. An apparatus for detecting presence/absence of a foreign substance on a substrate held on a stage through a chuck, the apparatus comprising:
a measurement device configured to measure a surface condition;
a second substrate different from the substrate; and
a processing unit configured to determine the presence/absence of a foreign substance based on a measurement result on a surface condition of the substrate obtained by the measurement device, cause the measurement device to measure a surface condition of the second substrate upon replacing the substrate on the chuck with the second substrate, if it is determined that a foreign substance exists, and determine whether an adhering location of the foreign substance is the substrate, based on a measurement result on the surface condition of the second substrate.

* * * * *